United States Patent
Reed et al.

(10) Patent No.: US 10,532,118 B2
(45) Date of Patent: Jan. 14, 2020

(54) STERILIZATION SYSTEM FOR A BLOW/FILL/SEAL MACHINE

(71) Applicant: Weiler Engineering, Inc., Elgin, IL (US)

(72) Inventors: Charles H. Reed, Denver, NC (US); Andrew W. Goll, Huntley, IL (US); Jeffrey D. Stanley, Cary, IL (US)

(73) Assignee: Weiler Engineering, Inc., Elgin, IL (US)

( * ) Notice: Subject to any disclaimer, the term of this patent is extended or adjusted under 35 U.S.C. 154(b) by 0 days.

(21) Appl. No.: 16/279,126

(22) Filed: Feb. 19, 2019

(65) Prior Publication Data

US 2019/0201567 A1 Jul. 4, 2019

Related U.S. Application Data

(60) Division of application No. 15/214,853, filed on Jul. 20, 2016, now Pat. No. 10,335,507, which is a continuation-in-part of application No. PCT/US2015/011916, filed on Jan. 19, 2015.

(60) Provisional application No. 61/929,374, filed on Jan. 20, 2014.

(51) Int. Cl.
| | |
|---|---|
| *A61L 2/20* | (2006.01) |
| *B29C 49/42* | (2006.01) |
| *B29C 49/46* | (2006.01) |
| *C01B 21/36* | (2006.01) |

(52) U.S. Cl.
CPC .............. *A61L 2/20* (2013.01); *B29C 49/4273* (2013.01); *B29C 49/46* (2013.01); *C01B 21/36* (2013.01); *A61L 2202/14* (2013.01); *A61L 2202/23* (2013.01); *B29C 2049/4635* (2013.01); *B65B 2210/08* (2013.01)

(58) Field of Classification Search
CPC ........ A61L 2/20; B29C 49/46; B29C 49/4273
See application file for complete search history.

(56) References Cited

U.S. PATENT DOCUMENTS

2011/0085938 A1* 4/2011 Carbone ............... A61L 2/0094
422/29

* cited by examiner

*Primary Examiner* — Kevin Joyner
(74) *Attorney, Agent, or Firm* — Olson & Cepuritis, Ltd.

(57) ABSTRACT

A fill assembly sterilization method and system for a blow/fill/seal machine utilizes a closed loop circulation of sterilant containing gas. A typical sterilant is nitrogen dioxide in humidified air. The closed loop includes a shroud that defines a plenum and encloses the fill system. Optionally, at least one high efficiency particulate absorption (HEPA) filter is provided in the closed loop. Sterility assurance level of $10^{-6}$ can be achieved by subjecting the fill system to the sterilizing gas for at least 20 minutes at a temperature in the range of about 18° C. to about 30° C. Preferred sterilant gas is humidified air containing about 10 to about 20 milligrams of nitrogen dioxide per liter.

5 Claims, 2 Drawing Sheets

STERILIZATION SYSTEM FOR A
BLOW/FILL/SEAL MACHINE

CROSS-REFERENCE TO RELATED
APPLICATIONS

This application is a division of U.S. patent application Ser. No. 15/214,853, filed on Jul. 20, 2016, which, in turn, is a continuation-in-part of PCT/US2015/011916, filed on Jan. 19, 2015, and claims the benefit of U.S. Provisional Application No. 61/929,374, filed on Jan. 20, 2014, all incorporated herein by reference in their entireties.

FIELD OF INVENTION

This invention relates to blow/fill/seal machines and aseptic packaging utilizing such machines.

BACKGROUND OF THE INVENTION

Blow/fill/seal machines are commonly used for aseptic packaging of pharmaceutical products; especially biologicals, proteins, and like substances. To ensure aseptic packaging conditions, the product path and fill assemblies of these machines must be sterilized from time to time. Such sterilization usually is effected by high pressure steam at 110° C. to 125° C.; however, the available steam sterilization techniques are cumbersome and time consuming when applied to larger open volumes.

SUMMARY OF INVENTION

A sterilization system for a blow/fill/seal machine includes a shroud around a container fill assembly of the machine, defining a plenum, which is in confined flow communication with an external sterilization gas conduit.

The shroud together with the gas conduit and optionally at least one high efficiency particulate absorption (HEPA) filter define a closed loop in which a sterilizing gas is circulated.

In particular, the sterilization system comprises a shroud that encloses the fill assembly, and defines a sterilizing gas inlet and a sterilizing gas outlet. An external conduit defines at least one sterilizing gas flow passageway between the sterilizing gas inlet and the sterilizing gas outlet. A blower is provided in the external conduit adjacent to the sterilizing gas inlet for circulating the sterilizing gas through the shroud and the optional one or more HEPA filter(s), situated in the sterilizing flow passageway between the blower and the sterilizing gas inlet of the shroud. A sterilizing gas source in flow communication with the blower supplies a sterilizing gas comprising a sterilant such as nitrogen dioxide, chlorine dioxide, vaporized hydrogen peroxide, and the like to the sterilization system.

Preferably, sterilization of the fill assembly and its shroud is achieved by combining humidified air at a relative humidity of about 50% to about 75% with nitrogen dioxide to provide a sterilizing gas containing about 10 to about 20 milligrams of nitrogen dioxide per liter of the sterilizing gas, and contacting the fill assembly shroud with the sterilizing gas for a time period of at least 20 minutes at a temperature in the range of about 18° C. to about 30° C. Thereafter residual nitrogen dioxide is removed by sweeping the fill assembly with air at a temperature of at least 50° C. (about 122° F.) for at least 20 minutes, preferably about 30 to about 45 minutes, depending on shroud volume and fill assembly geometry.

DESCRIPTION OF PREFERRED
EMBODIMENTS

Blow/fill/seal technology is a specialized aseptic liquid packaging technology which refers to a particular container manufacturing technique where a container is formed from a thermoplastic material, filled, and sealed in a continuous process without human intervention. The filling and sealing of the container takes place in a sterile, enclosed space inside a blow/fill/seal machine. Typical illustrative fill assemblies are shown in U.S. Pat. No. 4,671,762 to Weiler et al. and U.S. Pat. No. 4,997,014 to Weiler et al., and are incorporated herein by reference in their entirety. The blow/fill/seal manufacturing technique provides an automated aseptic packaging process under controlled conditions in three steps: container sterilization, aseptic filling and container sealing.

At first a thermoplastic resin such as polypropylene, polyethylene, and the like, is extruded into a tubular shape (a parison) what ultimately becomes the final container. After a parison of desired length is extruded between open mold parts, the mold parts are closed, and a parison segment is cut from the extruded parison. Top of the parison segment is held in place and open, and the bottom of the parison is pinched shut by the closed mold parts. The parison segment and the mold are then moved to a filling zone where the fill assembly, comprising one or more blowing and filling nozzles, is located.

The blowing and filling nozzles are then lowered into the parison segment until a seal is formed between the parison segment and the neck of the mold. Sterile, filtered compressed air is introduced into the parison segment, expanding the parison segment against the mold cavity and forming a container body. After the blowing cycle is completed, the sterile air is vented from the container body and a sterile liquid product is metered into the container through a filling nozzle. When the filling cycle is complete, the filling nozzle is retracted and separate sealing molds close the top of the parison segment and seal the formed and filled container.

Figure 1:
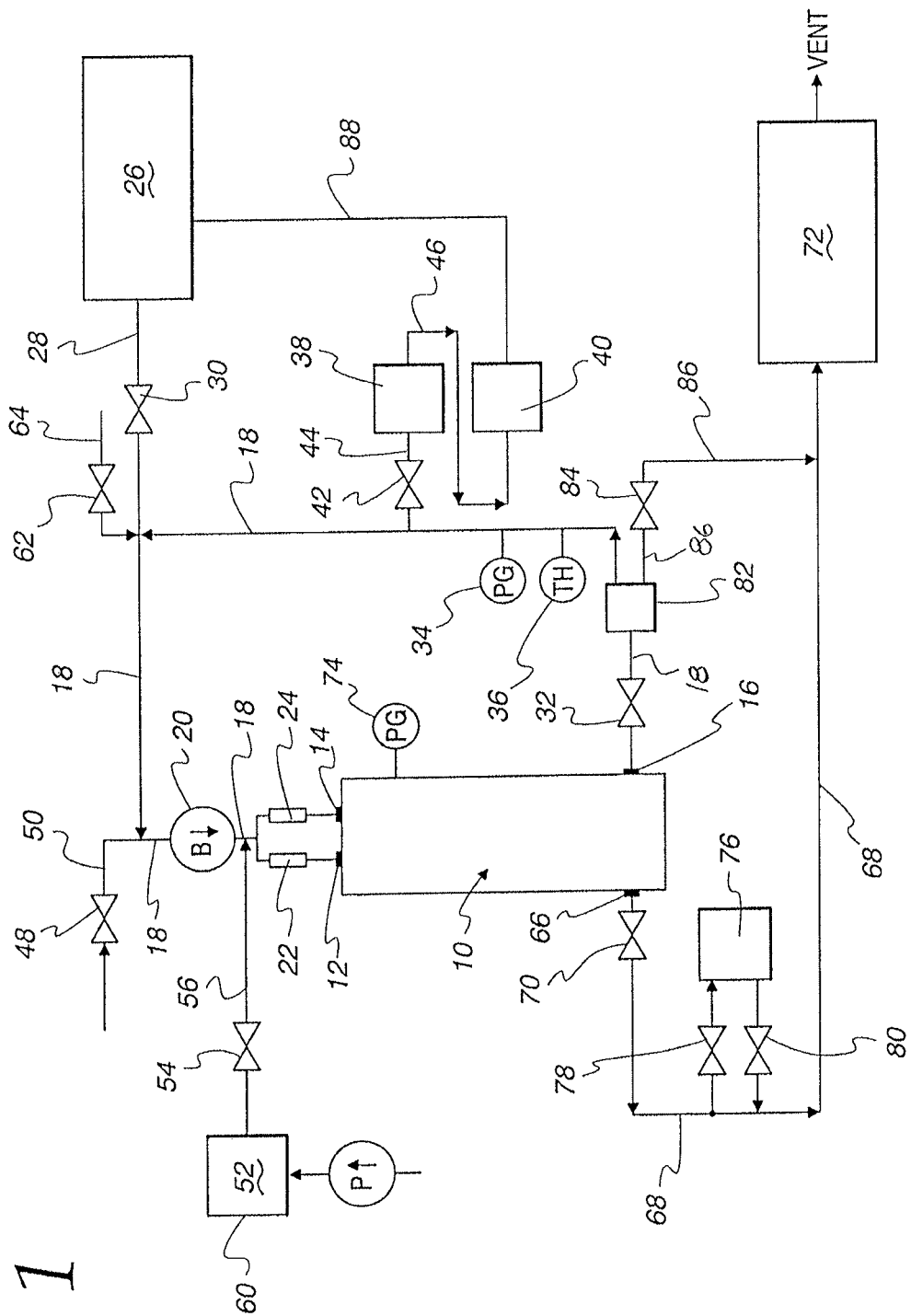
FIG. 1 is a schematic flow diagram illustrating an embodiment of the present blow/fill/seal machine sterilizing system.

The fill assembly of the blow/fill/seal machine has to be sterilized from time to time to assure aseptic filling conditions. Heretofore the sterilization process has been effected using a sanitization process for the shroud and internal steam sterilization for the product path. FIG. 1 illustrates an improved dry sterilization system for the shroud and the fill assembly enveloped by the shroud that can be utilized at relatively lower temperatures to achieve a sterility assurance level as high as $10^{-6}$ utilizing a sterilizing gas containing nitrogen dioxide and the like sterilant.

Referring to FIG. 1, shroud 10 encloses the fill assembly (not shown) of a blow/fill/seal machine and defines a plenum, sterilizing gas inlets 12 and 14, as well as sterilizing gas outlet 16 which is in confined flow communication with external conduit 18.

Blower 20 in external conduit adjacent to sterilizing gas inlets 12 and 14 serves to circulate the sterilizing gas through shroud 10. High efficiency particulate absorption (HEPA) filters 22 and 24 are situated between blower 20 and a pair of sterilizing gas inlets 12 and 14. While a single HEPA filter in the circulating sterilizing gas loop is adequate, in order to minimize pressure drop across the HEPA filter, two or more HEPA filters in parallel are preferred.

Sterilant source 26, supplying a sterilant such as nitrogen dioxide, is connected to external conduit 18 and thus to blower 20 via a confined flow passageway defined by feed conduit 28, pneumatic valve 30, external conduit 18, as well as conduits 44, 46 and 88. Manifold 82 provides communication with a system pressure relief system which comprises conduit 86 and relief valve 84 in conduit 86. System pressure during a sterilization cycle usually does not exceed 150 Pascals, and relief valve 84 is set to open when system pressure exceeds that value. During normal sterilization cycle, pneumatic control valve 32 is open and a sterilizing gas containing nitrogen dioxide is circulated through HEPA filters 22, 24 and shroud 10 by the action of blower 20. Pressure gauge 34 and thermistor 36 in conduit 18 monitor pressure and temperature, respectively, of the circulating sterilizing gas in external conduit 18. Pressure gauge 74 monitors pressure within shroud 10.

Humidity sensor 38 and sterilant concentration sensor 40 are operably connected in series to conduit 18 via valve 42 in conduit 44 and by conduit 46. During a sterilization cycle a portion of the sterilizing gas flows through conduits 44, 46 and 88 and into feed conduit 28 which is in confined flow communication with conduit 18.

For effective sterilization, the sterilizing gas has to have a predetermined relative humidity (RH) in the range of about 50% RH to about 75% RH. The necessary humidity is provided by humidifier 52 via valve 54 conduit 56 which receives water from a convenient source (not shown) by the action of water pump 60.

Air combined with a sterilant such as nitrogen dioxide from source 26 constitutes the sterilizing gas. Any make-up air is supplied to the sterilization system, as needed, via valve 62 and conduit 64. Source 26 also supplies make-up sterilant, as needed, based on signal from sensor 40.

After completion of a sterilization cycle, purge air is introduced into the system via valve 48 in purge conduit 50 which is operably connected to external conduit 18 upstream from blower 20. Purge air is circulated through the sterilization system for at least 20 minutes, preferably at a temperature of about 65° C.

Purge air leaves the sterilization system from shroud 10 via purge air exit port 66 and exit conduit 68 controlled by valve 70, and enters scrubber 72 before being vented. Scrubber 72 removes residual sterilant such as nitrogen dioxide after the sterilization cycle has been completed. Sterilant sensor 76, operably connected to exit conduit 68 by valves 78 and 80, monitors sterilant concentration in exit conduit 68. Purge air is heated by heaters that can be situated around the HEPA filter housing, by conduction or convection derived heat resulting from steam sterilization of the product path within the fill assembly, or any other convenient manner.

Figure 2:
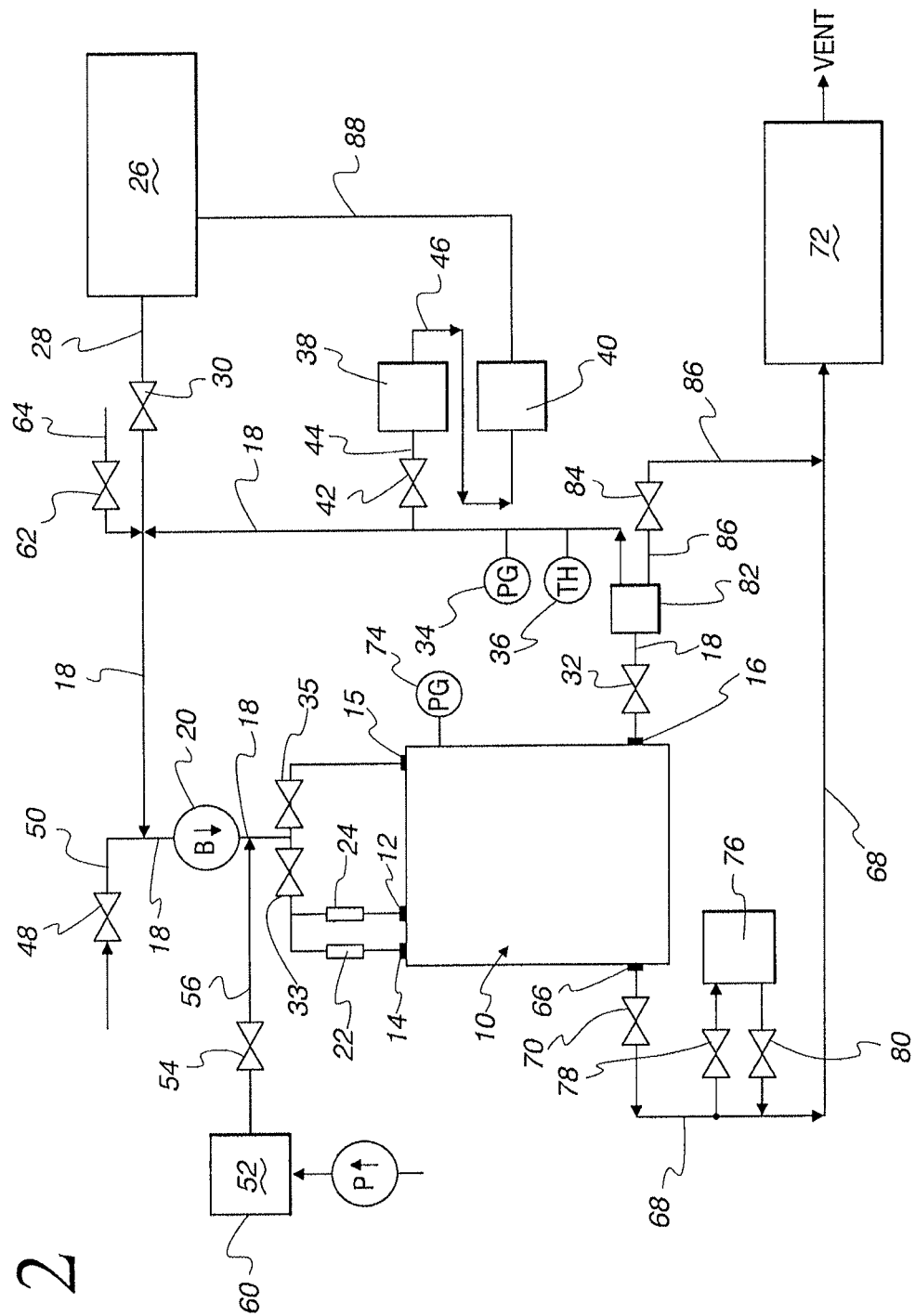
FIG. 2 is a schematic flow diagram illustrating another embodiment of the present blow/fill/seal machine sterilizing system.

Another embodiment of the sterilization system is shown in FIG. 2 in which the system components that are the same as those shown in FIG. 1 are identified by the same numerals. In the system shown in FIG. 2, however, HEPA filters 22 and 24 can be subjected to surface sterilization only, if desired, while a sterilizing gas is circulated through the rest of the system in the same manner as described with respect to FIG. 1. To that end, valve 33 upstream of HEPA filters 22 and 24 is closed and valve 35 is open permitting sterilizing gas flow directly into shroud 10 via sterilizing gas inlet 15. Alternatively, both valve 33 and valve 35 can be open, thereby providing a relatively higher sterilizing gas flow through shroud 10. In the latter case, a three-way valve (not shown) can be installed in lieu of valve 33 and valve 35.

The sterilizing gas is prepared for use by combining humidified air having a relative humidity of about 50% to about 75% with a sterilant such as nitrogen dioxide from a suitable source such as source 26. If nitrogen dioxide is the sterilant, the amount of nitrogen dioxide in the sterilizing gas is about 10 to about 20 milligrams per liter (mg/L) of the sterilizing gas.

During a sterilization cycle, the fill assembly is contacted by the sterilizing gas for at least 20 minutes at a temperature in the range of about 18° C. to about 30° C., preferably at ambient temperature, for 20 to about 30 minutes.

The foregoing discussion and the examples are intended as illustrative and are not to be taken as limiting. Still other variants and rearrangements of parts within the spirit and scope of the present invention are possible and will readily present themselves to those skilled in the art.

The invention is claimed is:

1. A method for sterilizing a fill assembly in a blow/fill/seal machine which comprises
    combining humidified air having a relative humidity of about 50% to about 75% with nitrogen dioxide to provide a sterilizing gas containing about 10 to about 20 milligrams of nitrogen dioxide per liter of the sterilizing gas;
    contacting the fill assembly with the sterilizing gas for a sterilization time period of at least 20 minutes at a temperature in the range of about 18° C. to about 30° C.; and
    thereafter sweeping the fill assembly with air at a temperature of at least 50° C. for a time period sufficient to remove residual nitrogen dioxide from the fill assembly.

2. The method in accordance with claim 1 wherein the fill assembly is swept with air at a temperature of at least 65° C.

3. The method in accordance with claim 1 wherein said sterilization time period is in the range of 20 minutes to 30 minutes.

4. The method in accordance with claim 1 wherein the sterilizing gas is passed through a HEPA filter before contacting the fill assembly.

5. The method in accordance with claim 1 wherein the fill assembly is swept with air for a time period in the range of about 30 minutes to about 45 minutes.

* * * * *